US008420833B2

(12) United States Patent
Katz et al.

(10) Patent No.: US 8,420,833 B2
(45) Date of Patent: Apr. 16, 2013

(54) PRODUCING BIOFUELS USING POLYKETIDE SYNTHASES

(75) Inventors: Leonard Katz, Oakland, CA (US); Jeffrey L Fortman, San Francisco, CA (US); Jay D Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 83 days.

(21) Appl. No.: 12/921,463

(22) PCT Filed: Apr. 29, 2009

(86) PCT No.: PCT/US2009/042132
§ 371 (c)(1),
(2), (4) Date: Sep. 28, 2010

(87) PCT Pub. No.: WO2009/134899
PCT Pub. Date: Nov. 5, 2009

(65) Prior Publication Data
US 2011/0021790 A1  Jan. 27, 2011

Related U.S. Application Data

(60) Provisional application No. 61/048,817, filed on Apr. 29, 2008.

(51) Int. Cl.
*C07D 309/00* (2006.01)
*C07D 313/00* (2006.01)
*C12P 17/08* (2006.01)
*C12P 7/06* (2006.01)
*C12N 9/40* (2006.01)

(52) U.S. Cl.
USPC ........... 549/273; 549/266; 435/124; 435/125; 435/136; 435/183

(58) Field of Classification Search .................. 549/273, 549/266; 435/124, 125, 136, 183
See application file for complete search history.

(56) References Cited

U.S. PATENT DOCUMENTS

| | | | |
|---|---|---|---|
| 3,839,378 A | | 10/1974 | Yamaguchi et al. |
| 5,234,719 A | * | 8/1993 | Richter et al. ............. 427/384 |
| 5,672,491 A | * | 9/1997 | Khosla et al. ............. 435/148 |
| 5,712,146 A | | 1/1998 | Khosla et al. |
| 5,830,750 A | | 11/1998 | Khosla et al. |
| 5,843,718 A | | 12/1998 | Khosla et al. |
| 6,303,342 B1 | | 10/2001 | Julien et al. |
| 6,639,089 B2 | | 10/2003 | Ito et al. |
| 6,939,845 B2 | | 9/2005 | Gautschi et al. |
| 7,198,922 B2 | | 4/2007 | Leadlay et al. |

FOREIGN PATENT DOCUMENTS

| | | |
|---|---|---|
| WO | WO 97/02358 A1 | 1/1997 |
| WO | WO 98/49315 A2 | 11/1998 |
| WO | WO 2006/024502 A2 | 3/2006 |
| WO | WO 2007/129770 A2 | 11/2007 |
| WO | WO 2009/121066 A2 | 10/2009 |

OTHER PUBLICATIONS anonymous: "Fatty acids," wayback, Mar. 15, 2008, retrieved from the internet: http://web.archive.org/web/20080315163005/http://www.cyberlipid.org/fa/acid0001.htm.
Ballini, R., et al., "A new synthesis of (±)-phoracantholide, (±)-dihydrorecifeiolide, and (±)-muscone via α-nitro ketones," *Liebigs Annalen*, vol. 1995(7), pp. 1381-1383 (Jul. 1, 1995).
Bisang et al.; "A chain initiation factor common to both modular and aromatic polyketide synthases," *Nature*, vol. 401, pp. 502-505 (1999).
Bush, K., et al., "Izumenolide—a novel β-lactamase inhibotor produced by Micromonospora. II. Biological properties," *The Jounal of Antiboitics*, vol. 33(11), pp. 1262-1269 (Nov. 1, 1980).
Clyne, D., et al., "They Synthesis of 14-Membered Macrocyclic Ethers," *Tetrahedron*, vol. 55(48), pp. 13659-13682 (Nov. 26, 1999).
Supplementary European Search Report from EP 09724907.2. (3 pages), Jul. 2, 2012.
Supplementary European Search Report from EP 09739701.2 (11 pages), Jul. 2, 2012.
Erb et al.; "Synthesis of C5-dicarboxylic acids from C2-units involving crotonyl-CoA carboxylase/reductase: the ethylmalonyl-CoA pathway," *Proc. Natl. Acad. Sci. U.S.A.*; 104(25):10631-10636 (Jun. 2007, Epub Jun. 4, 2007).
Hatcher, M., et al., "New silicon-mediated ring expansion of n-sized conjugated cycloalkenones into homoallylic n+3 lactones," *Tetrahedron Letters*, vol. 44(29), pp. 5407-5409 (Jul. 14, 2003).
Heathcote et al.; "Role of type II thioesterases: evidence for removal of short acyl chains produced by aberrant decarboxylation of chain extender units," *Chem Biol.*, vol. 8, No. 2, pp. 207-220 (2001).
Jacobsen et al.; "Precursor-Directed Biosynthesis of Erythromycin by Analogs by an Engineered Polyketide Synthase," *Science*, vol. 277, pp. 367-369 (1997).
van Buijtenen, J., et al., "Switching from S- to R-selectivity in the *Candida antarctica* lipase B-catalyzed ring-opening of omega-methylated lactones: tuning polymerizations by ring size," *Journal of the American Chemical Society*, vol. 129(23) (Jun. 1, 2007).

* cited by examiner

*Primary Examiner* — Nizal Chandrakumar
(74) *Attorney, Agent, or Firm* — Kilpatrick Townsend & Stockton LLP

(57) ABSTRACT

The present invention provides for a non-naturally occurring polyketide synthase (PKS) capable of synthesizing a carboxylic acid or a lactone, and a composition such that a carboxylic acid or lactone is included. The carboxylic acid or lactone, or derivative thereof, is useful as a biofuel. The present invention also provides for a recombinant nucleic acid or vector that encodes such a PKS, and host cells which also have such a recombinant nucleic acid or vector. The present invention also provides for a method of producing such carboxylic acids or lactones using such a PKS.

17 Claims, 6 Drawing Sheets

| Precursor | Structure generated in polyketide and name of Module | | | |
|---|---|---|---|---|
| acetyl CoA | srm LM S1 | | | |
| propionyl CoA | ery LM S2 | | | |
| malonyl CoA | ave Mod3 (ave3) A | ave Mod4 (ave4) ave Mod5 (ave5) B | srm Mod2 (srm2) C | nys Mod5 (nys5) olm Mod 3 (olm3) D |
| methylmalonyl CoA | pik Mod6 (pik6) ery Mod3 (ery) E | tyl Mod1 (tyl1) ery Mod2 (ery2) ery Mod1 (ery1) nys Mod2 (nys2) F | tyl Mod2 (tyl2) G | rap Mod1 (rap1) ery Mod4 (ery4) H |
| ethylmalonyl CoA | FK520 Mod4 FK4 I | | | tyl Mod5 (tyl5) olm Mod7 (olm7) J |

SpinosynLD-mod1-nysmod5-eryTE

TylosinLD-Mod1-nysmod5-eryTE

SpinosynLD-Mod1-eryMod4-eryTE

TylosinLD-Mod1-eryMod4-eryTE

PRODUCING BIOFUELS USING POLYKETIDE SYNTHASES

CROSS-REFERENCE TO RELATED APPLICATIONS

This application is the U.S. National Stage of International Application No. PCT/US2009/042132, filed Apr. 29, 2009, which claims priority to U.S. Provisional Patent Application Ser. No. 61/048,817, filed Apr. 29, 2008, hereby incorporated by reference.

STATEMENT OF GOVERNMENTAL SUPPORT

This invention was made with government support under Contract No. DE-AC02-05CH11231 awarded by the U.S. Department of Energy and under Award No. 0540879 awarded by the National Science Foundation. The government has certain rights in the invention.

FIELD OF THE INVENTION

This invention relates generally to biofuel production using polyketide synthases.

BACKGROUND OF THE INVENTION

Petroleum derived fuels have been the primary source of energy for over a hundred years. Petroleum, however, has formed over millions of years in nature and is not a renewable source of energy. A significant amount of research in alternative fuels has been ongoing for decades. Within this field, ethanol has been studied intensively as a gasoline substitute and the use of ethanol as transportation fuel has been increasing recently (Gray et al., *Curr Opin Chem Biol* 2006, 10:141). However, the efficiency of ethanol as a fuel is still in debate (Pimentel, *Natural Resources Research* 2005, 14:65; Farrell et al., *Science* 2006, 311:506). There is interest to design several potential alternative fuel molecules other than ethanol, which can be produced biosynthetically, and to develop the biosynthetic pathways for enhanced production of the target fuel molecules using synthetic biology.

This present invention involves the biosynthesis of carboxylic acids and lactones, which can be a source of renewable fuels, using polyketide synthases (PKS).

SUMMARY OF THE INVENTION

This present invention provides for a carboxylic acid or a lactone produced by a polyketide synthase (PKS). Such carboxylic acids or lactones can be polyketides of one or more ketide units, or 2, 3, 4, 5, or 6 or more ketide units. The carboxylic acid comprises one or more methyl and/or ethyl functional groups. The lactone is an even-numbered lactone ring comprising one or more methyl and/or ethyl functional groups.

The present invention provides for a carboxylic acid having the following chemical structure:

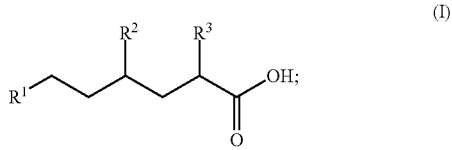

wherein $R^1$ is H or —$CH_3$; $R^2$ is H, —$CH_3$, or —$CH_2CH_3$; and, $R^3$ is H, —$CH_3$, or —$CH_2CH_3$; or $R^2$ and $R^3$ are each H, and $R^1$ is H, —$CH_3$, or —$(CH_2)_nCH_3$, wherein n is an integer from 1 to 6. In some embodiments of the invention, $R^1$ is H or —$CH_3$; $R^2$ is H, —$CH_3$, or —$CH_2CH_3$; and, $R^3$ is H, —$CH_3$, or —$CH_2CH_3$. In other embodiments of the invention, $R^2$ and $R^3$ are each H, and $R^1$ is H, —$CH_3$, or —$(CH_2)_nCH_3$, wherein n is an integer from 1 to 6. In particular embodiments of the invention, $R^2$ and $R^3$ are each H, and $R^1$ is —$(CH_2)_nCH_3$, wherein n is an integer from 1 to 6

The present invention provides for a lactone having the following chemical structure:

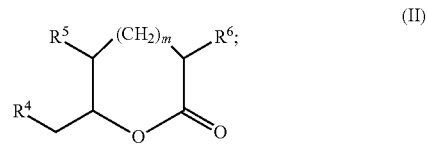

wherein $R^4$ is H or —$CH_3$; $R^5$ and $R^6$ are each independently H, —$CH_3$, or —$CH_2CH_3$; and m is 1, 3, 5, 7 or 9; with the proviso that when m is 1 then $R^5$ and $R^6$ are each independently H, —$CH_3$, or —$CH_2CH_3$, and when m is 3, 5, 7 or 9 then $R^4$ is H or —$CH_3$, $R^5$ and $R^6$ are each H.

The present invention provides for a polyketide synthase (PKS) capable of synthesizing a carboxylic acid or a lactone. Such carboxylic acids or lactones include the carboxylic acids and lactones of the present invention. Such carboxylic acids or lactones include the carboxylic acids described in Tables 1 and 2, and the lactones described in Tables 3-7.

The present invention provides for a recombinant nucleic acid that encodes a polyketide synthase (PKS) of the present invention. The present invention also provides for a vector or expression vector comprising a recombinant nucleic acid of the present invention. The present invention provides for a host cell comprising any of the recombinant nucleic acid and/or PKS of the present invention.

The present invention provides a method of producing a carboxylic acid, such as a carboxylic acid described in Tables 1 and 2, comprising: providing a host cell of the present invention, and culturing said host cell in a suitable culture medium such that the carboxylic acid is produced. The method can further comprise isolating said carboxylic acid from the host cell and/or the culture medium. The method can further comprise reacting the isolated carboxylic acid with an alcohol to produce an ester.

The present invention provides a method of producing a carboxylic acid, such as a carboxylic acid chosen from the group consisting of compounds 1 to 53, comprising: providing a host cell of the present invention, and culturing said host cell in a suitable culture medium such that the carboxylic acid is produced. The method can further comprise isolating said carboxylic acid from the host cell and/or the culture medium. The method can further comprise reacting the isolated carboxylic acid with an alcohol to produce an ester.

The present invention provides a method of producing a lactone, such as a lactone described in Tables 3-7, comprising: providing a host cell of the present invention, and culturing said host cell in a suitable culture medium such that the lactone is produced. The method can further comprise isolating said lactone from the host cell and/or the culture medium.

The present invention provides for a composition comprising a carboxylic acid or lactone, or an ester derived from the carboxylic acid, isolated from a host cell, from which the carboxylic acid or lactone was produced, and/or the culture medium, and trace residues and/or contaminants of the host cell and/or the culture medium.

The carboxylic acid or lactone of the present invention, or derivative thereof, is useful as a biofuel.

BRIEF DESCRIPTION OF THE DRAWINGS

The foregoing aspects and others will be readily appreciated by the skilled artisan from the following description of illustrative embodiments when read in conjunction with the accompanying drawings.

FIG. 1 shows the types of modules employed and corresponding precursors utilized for incorporation into polyketide chains. Loading modules are designated S1 and S2. The remaining compounds represent the structures incorporated into the growing polyketide chain employing extender modules A-J. The dashed line indicates the C—C bond formed through Claisen condensation; atoms to the right of the bond and the C atom at the left of the dashed line represent the structures determined by the module employed. The R group represents the existing acyl chain prior to incorporation determined by the module. Abbreviations: ave, avermectin; ery, erythromycin; FK, ascomycin (FK520); LM, loading module; Mod, module; nys, nystatin; olm, oligomycin; pik, pikromycin; srm, spiramycin; tyl, tylosin. Structures generated and modules used in this proposal are highlighted in blue.

DETAILED DESCRIPTION

Figure 2:
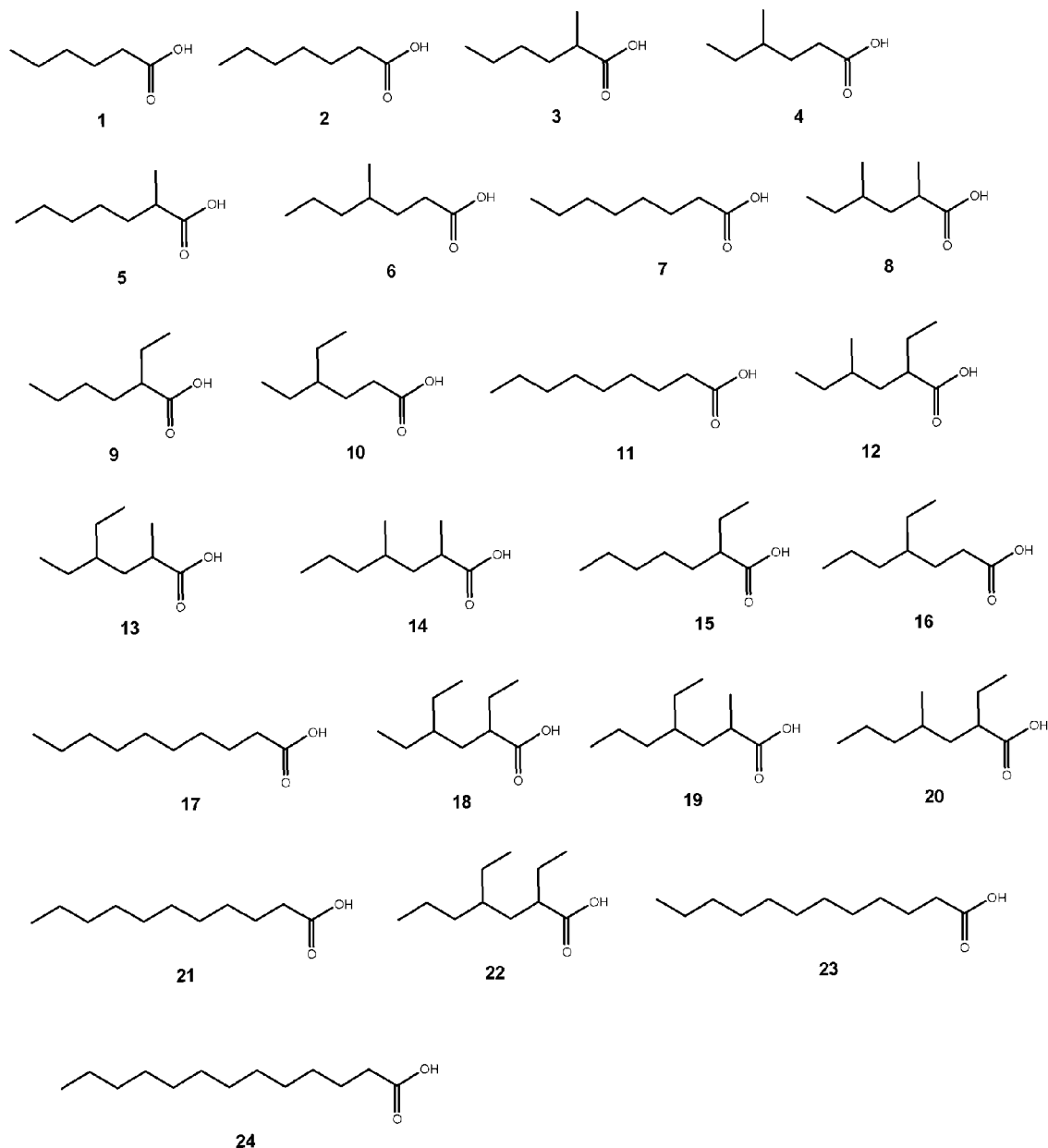
FIG. 2 shows reduced short-and medium chain polyketides (fatty acids) containing 6-13 carbon atoms.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a carboxylic acid" includes a plurality of such carboxylic acids, and so forth.

In this specification and in the claims that follow, reference will be made to a number of terms that shall be defined to have the following meanings:

The terms "expression vector" or "vector" refer to a compound and/or composition that can be introduced into a host cell by any suitable method, including but not limited to transduction, transformation, transfection, infection, electroporation, conjugation, and the like; thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "isolated" refers to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA.

The term "operably linked" refers to a functional linkage between a nucleic acid expression control sequence (such as a promoter) and a second nucleic acid sequence, wherein the expression control sequence directs transcription of the nucleic acid corresponding to the second sequence.

These and other objects, advantages, and features of the invention will become apparent to those persons skilled in the art upon reading the details of the invention as more fully described below.

Carboxylic Acids (Fatty Acids)

The present invention provides for a carboxylic acid comprising one or more methyl and/or ethyl functional groups, wherein the carboxylic acid is produced by a PKS.

The present invention provides for a carboxylic acid having the following chemical structure:

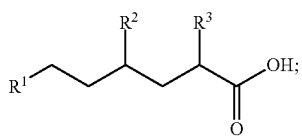

Figure 8:
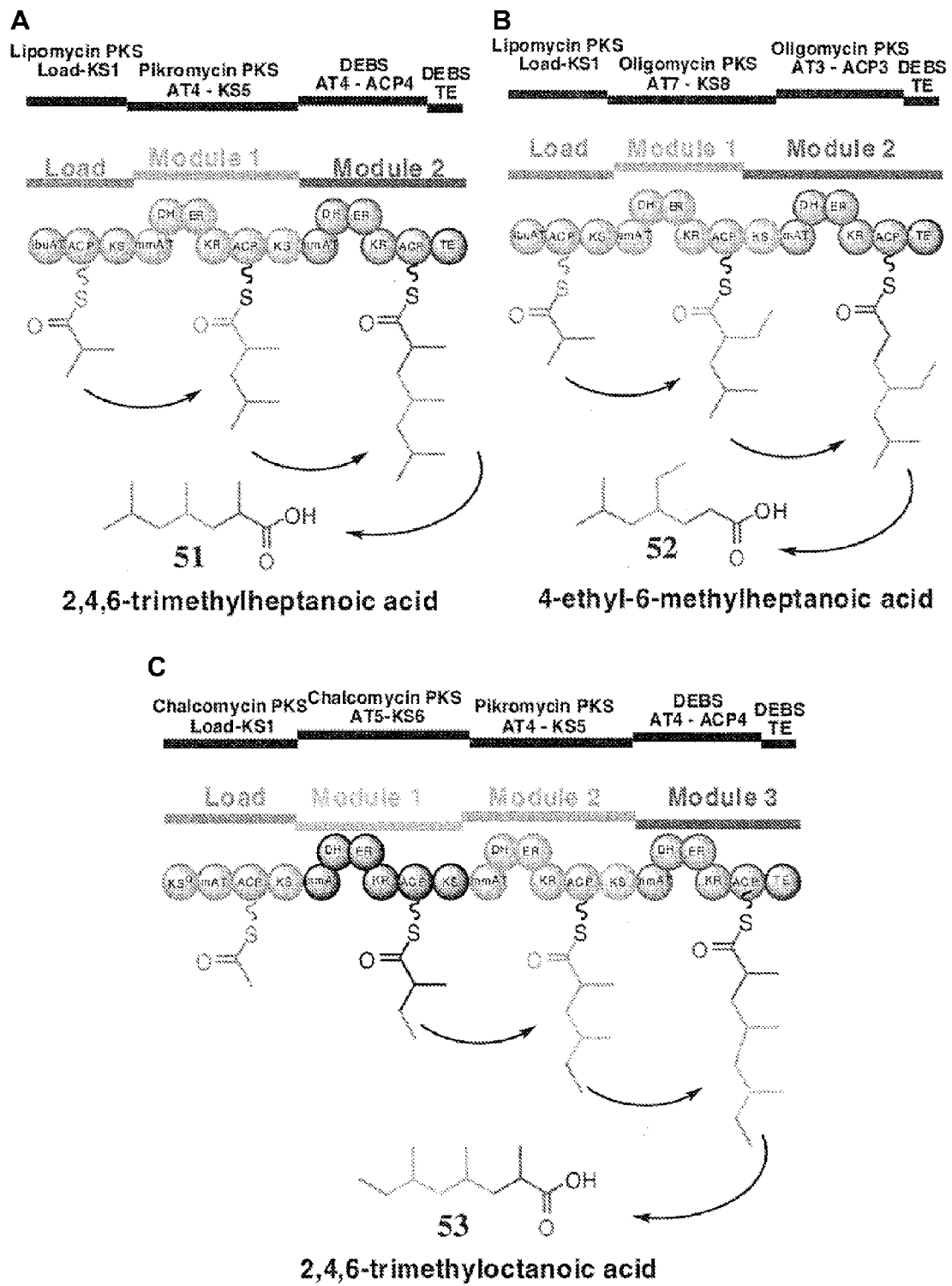
FIG. 8 shows exemplary PKSs for synthesizing compounds 51, 52, and 53.

(I)

wherein $R^1$ is H or —$CH_3$; $R^2$ is H, —$CH_3$, or —$CH_2CH_3$; and, $R^3$ is H, —$CH_3$, or —$CH_2CH_3$; or $R^2$ and $R^3$ are each H, and $R^1$ is H, —$CH_3$, or —$(CH_2)_nCH_3$, wherein n is an integer from 1 to 6. In some embodiments of the invention, $R^1$ is H or —$CH_3$; $R^2$ is H, —$CH_3$, or —$CH_2CH_3$; and, $R^3$ is H, —$CH_3$, or —$CH_2CH_3$. In other embodiments of the invention, $R^2$ and $R^3$ are each H, and $R^1$ is H, —$CH_3$, or —$(CH_2)_nCH_3$, wherein n is an integer from 1 to 6. In particular embodiments of the invention, $R^2$ and $R^3$ are each H, and $R^1$ is —$(CH_2)_nCH_3$, wherein n is an integer from 1 to 6. The present invention provides for a carboxylic acid having a chemical structure as indicated in Tables 1 and 2, and FIG. 8.

Lactones

The present invention provides for a lactone having an even-numbered lactone ring comprising one or more methyl and/or ethyl functional groups, wherein the lactone is produced by a PKS.

The present invention provides for a lactone having the following chemical structure:

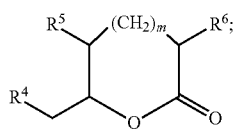

(II)

wherein $R^4$ is H or —$CH_3$; $R^5$ and $R^6$ are each independently H, —$CH_3$, or —$CH_2CH_3$; and m is 1, 3, 5, 7 or 9; with the proviso that when m is 1 then $R^5$ and $R^6$ are each independently H, —$CH_3$, or —$CH_2CH_3$, and when m is 3, 5, 7 or 9 then $R^4$ is H or —$CH_3$, $R^5$ and $R^6$ are each H. The present invention provides for a lactone having a chemical structure as indicated in Tables 3-7.

The present invention provides for a six-membered lactone having the following chemical structure:

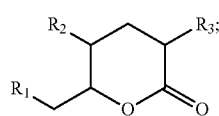

(III)

wherein $R^1$ is H or —$CH_3$; $R^2$ and $R^3$ are each independently H, —$CH_3$, or —$CH_2CH_3$. The present invention provides for a six-membered lactone having a chemical structure as indicated in Table 3.

The present invention provides for an eight-membered lactone having the following chemical structure:

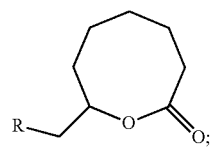

(IV)

wherein R is H or —$CH_3$. The present invention provides for an eight-membered lactone having a chemical structure as indicated in Table 4.

The present invention provides for a ten-membered lactone having the following chemical structure:

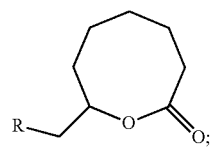

(V)

wherein R is H or —$CH_3$. The present invention provides for a ten-membered lactone having a chemical structure as indicated in Table 5.

The present invention provides for a twelve-membered lactone having the following chemical structure:

(VI)

wherein R is H or —$CH_3$. The present invention provides for a twelve-membered lactone having a chemical structure as indicated in Table 6.

The present invention provides for a fourteen-membered lactone having the following chemical structure:

(VII)

wherein R is H or —$CH_3$. The present invention provides for a fourteen-membered lactone having a chemical structure as indicated in Table 7.

Polyketide Synthases (PKS)

The present invention provides for a polyketide synthase (PKS) capable of synthesizing a carboxylic acid or a lactone.

Such carboxylic acids or lactones include the carboxylic acids and lactones of the present invention. Such carboxylic acids or lactones include the carboxylic acids described in Tables 1 and 2, and compounds 51-53, and the lactones described in Tables 3-7. The PKS modules sufficient for synthesizing each specific carboxylic acid or lactone of the resent invention are described in Tables 1-7. The PKS is not naturally occurring. In some embodiments, the PKS is a hybrid PKS comprising of a combination of naturally occurring modules which in nature are not found in this combination.

The PKS can be located in a host cell, or isolated or purified. The PKS can synthesize the carboxylic acid or lactone in vivo (in a host cell) or in vitro (in a cell extract or where all necessary chemical components or starting materials are provided). The present invention provides methods of producing the carboxylic acid or lactone using any of these in vivo or in vitro means. For example, carboxylic acid compound 1 can be synthesized using a PKS comprising the modules 51 (srm LM), D (nys Mod5 or olm Mod3), and D (nys Mod5 or olm Mod3) (see Table 1 and FIG. 1). For example, lactone compound 26 can be synthesized using a PKS comprising the modules 51 (srm LM), B (ave Mod4 or ave Mod5), and D (nys Mod5 or olm Mod3) (see Table 3 and FIG. 1).

The goal of this project is to employ type I, modular polyketide synthases (PKS) to produce a number of selected short- and medium-chain fatty acids (or their corresponding lactones). These molecules can be used as starting materials for conversion into biofuels. In general, short- and medium-chain polyketides with diversities in chemical structures can be generated from modular PKSs, but the best compounds to be converted to biofuels are those which are the most reduced. Hence, only highly reduced molecules will be considered in this proposal. Compounds containing double bonds or keto groups will not be described. Compounds containing a single hydroxy group can form lactones, hence they will be reviewed.

Polyketides are produced by polyketide synthases via decarboxylative Claisen condensation of acyl units that consist of short chain fatty acids (in the form of CoA). Unlike fatty acid synthases which utilize acetyl CoA as the starter and malonyl CoA as the extender units, PKSs can utilize a number of different starters (e.g. acetyl CoA, propionyl CoA) and extenders, some of which contain stereospecific methyl or ethyl side chains. For the purposes of this proposal, the chirality of the methyl or ethyl side chains in the compounds described will not be considered. In addition, PKSs do not always reduce the 3-carbonyl formed from condensation but may leave it either unreduced (ketone), partially reduced (hydroxyl, 2,3-ene) or fully reduced (3-methylene). The structure (and chirality) of the α-carbon and β-carbonyl is determined by the module of the PKS employed in the synthesis of the growing chain at each particular step. FIG. 1 shows the various modules employed to give rise to the range of structures possible and the precursor utilized by each module for incorporation into the nascent acyl (polyketide) chain.

Chain length is determined by the number of condensations that take place, which in turn is determined by the number of modules employed. All chain growth uses a starter determined by the loading module, typically contributing two (S1) or three (S2) carbon atoms to the overall length of the acyl chain. Each extender module contributes two carbons to the backbone but also may contribute additional carbons as side chains. Thus a single condensation could yield a molecule with as few as 4 carbon atoms (modules S1 and D) and as many as seven (modules S2 and J). Two condensations generate a molecule that contains 6-11 carbons depending on the modules employed, but 6 or 7 carbon backbones. Similarly, three condensations will yield molecules with 8-14 carbon backbones.

The level of reduction is also determined by the modules employed. In general, if more reduced molecules are desired, modules D, J, or one from the H group should be used. If a hydroxyl is desired internally to enable the formation of a lactone, a module from the B or F group should be used. Lactone formation will occur if a PKS thioesterase domain (e.g. eryTE) is placed immediately downstream of the terminal external module.

Figure 3:
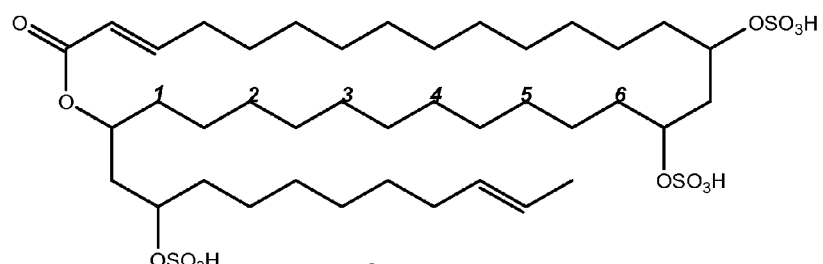
FIG. 3 shows the structure of Izumenolide. Numbers 1-6 refer to the atoms introduced by modules 1-6, respectively.

Interest in biofuels prompts the use of PKS modules that produce reduced fatty acids (see FIG. 1, modules S1, S2, B D, F, H, and J). Twenty-four such fully reduced fatty acids are shown that are composed of 6-13 carbon atoms. Compounds 1-6, 8-10, 12-16, and 18-20, are generated as triketides from a loading module and two extender modules. They are produced as described in Table 1. The remaining molecules employ a loading domain and three or more extender modules. They can be produced employing modules from the Ize PKS involved in the synthesis of izumenolide (FIG. 3, compound 25), a reduced polyketide isolated from *Micromonospora chalcea* subsp. *izumensis*.

TABLE 1

Modules for the synthesis of reduced triketide fatty acids.
Modules are described in FIG. 1.

| Compound | Load | 1 | 2 |
| --- | --- | --- | --- |
| 1 | S1 | D | D |
| 2 | S2 | D | D |
| 3 | S1 | D | H |
| 4 | S1 | H | D |
| 5 | S2 | D | H |
| 6 | S2 | H | D |
| 8 | S1 | H | H |
| 9 | S1 | D | J |
| 10 | S1 | J | D |
| 12 | S1 | H | J |
| 13 | S1 | J | H |
| 14 | S2 | H | H |
| 15 | S2 | D | J |
| 16 | S2 | J | D |
| 18 | S1 | J | J |
| 19 | S2 | J | H |
| 20 | S2 | H | J |
| 22 | S2 | J | J |

Compounds 7, 11, 17, 21, 23, and 24 can be made by combining a loading module S1 or S2 with modules 2 through 5 (depending on the size of the molecule desired) of the Ize PKS, as outlined in Table 2. Ize modules 2 through 6 are anticipated to resemble module D but be sufficiently different from each other to coexist in a stable form and not undergo homologous recombination.

TABLE 2

Production of short- and medium chain unbranched fatty acids.

| Compound | Proposed Method of Construction |
| --- | --- |
| 7 | S1 + Ize Modules 2-4 |
| 11 | S2 + Ize Modules 2-4 |
| 17 | S1 + Ize Modules 2-5 |
| 21 | S2 + Ize Modules 2-5 |
| 23 | S1 + Ize Modules 2-6 |
| 24 | S2 + Ize Modules 2-6 |

Figure 4:
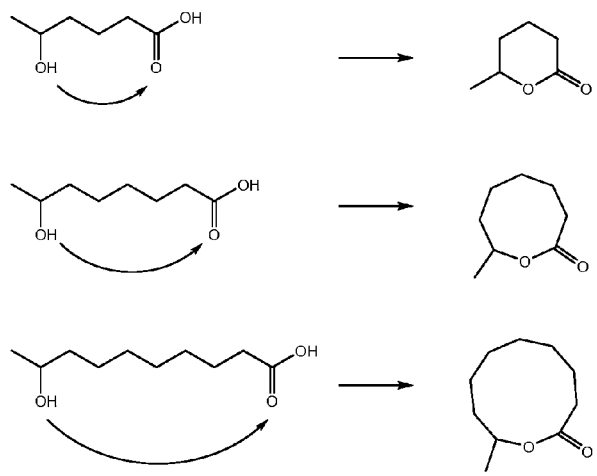
FIG. 4 shows thioesterase-directed formation of lactones from fatty acids.

Lactones containing an even number of ring atoms (6 minimum) can be produced from a PKS by the strategic placement of a hydroxyl group relative to the position of the terminal carbonyl function, as shown in FIG. 4. A lactone will form intracellularly if a TE (thioesterase) domain is placed 3' to the terminal module in the constructed PKS. The size of the lactone ring will be determined by the relative positions of the hydroxyl and the carbonyl. The PKS capable of producing the lactones described in Tables 3-7 all further comprise a TE (thioesterase) domain is placed 3' to the terminal module in PKS.

Although many additional compounds can be made as 6-membered lactones, we will only consider the formation of compounds 26-37. These arise through assembly of a loading domain and two modules as outlined in Table 3. Module 1 contains a ketoreductase domain to enable production of the necessary hydroxyl for lactone formation. An alternative method to produce 32 is to use the naturally occurring loading domain and the first two modules of the spinosyn PKS.

TABLE 3

Production of six-membered lactone rings.

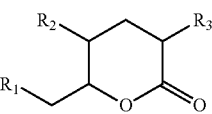

| | | | | Module | | Alternative method of synthesis |
|---|---|---|---|---|---|---|
| | $R_1$ | $R_2$ | $R_3$ | Load | 1 | 2 | |
| 26 | H | H | H | S1 | B | D | |
| 27 | H | H | $CH_3$ | S1 | B | H | |
| 28 | H | H | $CH_2CH_3$ | S1 | B | J | |
| 29 | H | $CH_3$ | H | S1 | F | D | |
| 30 | H | $CH_3$ | $CH_3$ | S1 | F | H | |
| 31 | H | $CH_3$ | $CH_2CH_3$ | S1 | F | J | |
| 32 | H | $CH_2CH_3$ | H | S1 | J | D | |
| 33 | H | $CH_2CH_3$ | $CH_3$ | S1 | J | H | |
| 34 | H | $CH_2CH_3$ | $CH_2CH_3$ | S1 | J | J | |
| 32 | $CH_3$ | H | H | S2 | B | D | Spn PKS: Load, Mod 1, Mod 2 |
| 35 | $CH_3$ | H | $CH_3$ | S2 | B | H | |
| 36 | $CH_3$ | H | $CH_2CH_3$ | S2 | B | J | |
| 37 | $CH_3$ | $CH_3$ | H | S2 | F | D | |
| 38 | $CH_3$ | $CH_3$ | $CH_3$ | S2 | F | H | |
| 39 | $CH_3$ | $CH_3$ | $CH_2CH_3$ | S2 | F | J | |
| 40 | $CH_3$ | $CH_2CH_3$ | H | S2 | J | D | |
| 41 | $CH_3$ | $CH_2CH_3$ | $CH_3$ | S2 | J | H | |
| 42 | $CH_3$ | $CH_2CH_3$ | $CH_2CH_3$ | S2 | J | J | |

Lactones containing eight or more atoms (38-45) can be made by the assembly of a starter module (S1 or S2) and three or more successive extender modules. These molecules can be made by using modules 1 and the downstream adjacent modules from the Ize PKS with a loading domain S1 or S2, as described in Tables 4-7.

TABLE 4

Production of eight-membered lactone rings.

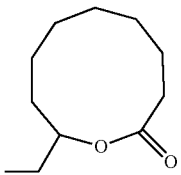

| | R | Method of Construction |
|---|---|---|
| 43 | H | S1 Loading domain + Ize Mod 1-3 |
| 44 | $CH_3$ | S2 Loading domain + Ize Mod 1-3 |

TABLE 5

Production of ten-membered lactone rings.

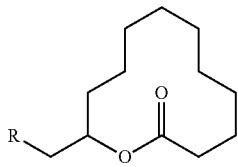

| | R | Method of Construction |
|---|---|---|
| 45 | H | S1 Loading domain + Ize Mod 1-4 |
| 46 | $CH_3$ | S2 Loading domain + Ize Mod 1-4 |

TABLE 6

Production of twelve-membered lactone rings.

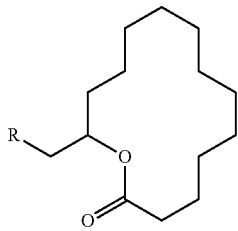

| | R | Method of Construction |
|---|---|---|
| 47 | H | S1 Loading domain + Ize Mod 1-5 |
| 48 | $CH_3$ | S2 Loading domain + Ize Mod 1-5 |

TABLE 7

Production of fourteen-membered lactone rings.

| | R | Method of Construction |
|---|---|---|
| 49 | H | S1 Loading domain + Ize Mod 1-6 |
| 50 | $CH_3$ | S2 Loading domain + Ize Mod 1-6 |

Polyketide synthases (PKS) employ short chain fatty acyl CoAs in Claisen condensation reactions to produce polyketides. Unlike fatty acid synthases which utilize acetyl CoA as the starter and malonyl CoA as the extender units, and use a single module iteratively to produce the nascent acyl chains, PKSs are composed of discrete modules, each catalyzing the chain growth of a single step. Modules can differ from each other in composition so that overall, a number of different starters (e.g. acetyl CoA, propionyl CoA) and extenders, some of which contain stereospecific methyl (or ethyl) side chains can be incorporated. In addition, PKS modules do not always reduce the 3-carbonyl formed from condensation but may leave it either unreduced (ketone), partially reduced (hydroxyl, 2,3-ene) or fully reduced (3-methylene). Many polyketide synthases employ malonyl CoA or [S]-2-methylmalonyl CoA as the starter for polyketide synthesis. In such cases the terminal carboxyl group is usually removed by a decarboxylase domain present at the N-terminus of the corresponding loading domain of the PKS. In summary, the structure (and chirality) of the α-carbon and β-carbonyl is determined by the module of the PKS employed in the synthesis of the growing chain at each particular step. Because of the correspondence between use of modules in the synthesis and the structure of the polyketide produced, it is possible to program the synthesis to produce a compound of desired structure by selection and genetic manipulation of polyketide synthases. FIG. 1 shows the various modules and the precursor utilized by each module for incorporation into the corresponding nascent acyl (polyketide) chain to give rise to the range of compounds of interest. FIG. 1 also provides a PKS source for each module. Each PKS source is well-known to one skilled in the art is readily available. In addition, for each module taught in FIG. 1, there may be other modules from other PKS that can be used.

Figure 5:
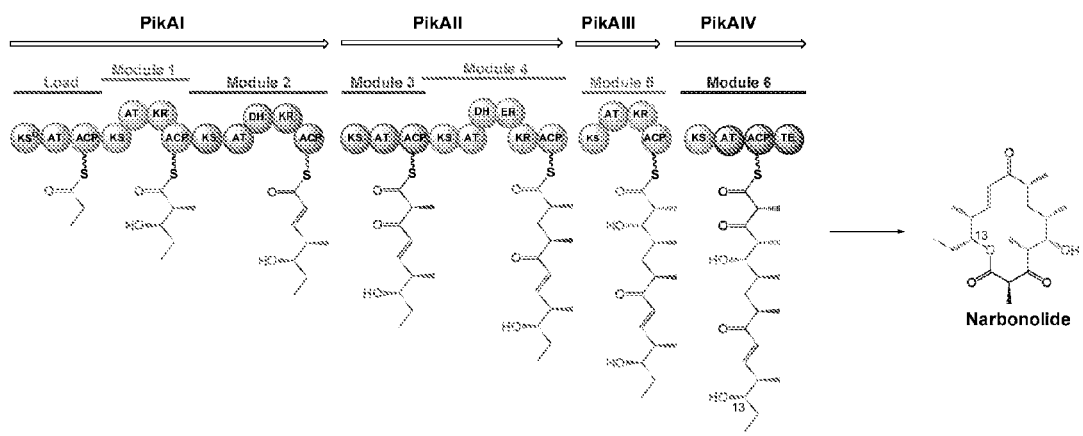
FIG. 5 shows the domain organization of the pik PKS and structures of proposed intermediates at the end of each condensation (and reduction) cycle. Linear polypeptides (Pik AI-AIV) are shown as open arrows; modules are indicated; domains are shown as spheres. Color-coding indicates the segment of the nascent polyketide chain corresponds to module and domains employing for programming. Abbreviations: ACP, acyl carrier protein; AT, acyltransferase; DH, dehydratase; ER, enoylreductase; KR, β-ketoreductase; KS, β-keto acyl-ACP synthase; $KS^Q$; KS domain lacking condensation activity but maintaining decarboxylation activity; TE, thioesterase.

All extender modules carry the β-acyl ACP synthase (commonly called the ketosynthase or KS) domain, which conducts the decarboxylative condensation step between the extender and the growing polyketide chain, and the acyl carrier protein (ACP) domain that carries the growing acyl chain and presents it to the cognate reductive domains for reduction of the β-carbonyl. Modules can differ from each other in composition so that a number of different starter and extender units, some of which contain stereospecific side chains (e.g. methyl, ethyl, propylene) can be incorporated. The acyltransferase (AT) domain of each module determines the extender unit (e.g. malonyl CoA, methylmalonyl CoA, etc.) incorporated. In addition, PKS modules do not always reduce the β-carbonyl formed from condensation but may leave it either unreduced (ketone), partially reduced (hydroxyl, 2,3-ene) or fully reduced (3-methylene), as shown in FIG. 1. The ketoreductase (KR) domain reduces the ketone to the OH function (stereospecifically); the dehydratase (DH) domain removes water from the α and β carbons leaving an α,β trans-double bond; the enoylreductase (ER) domain reduces the double bond to a β-methylene center; the reductive state of the β-carbonyl, therefore, is determined by the presence of functional reductive domains in the corresponding module. Less commonly, modules are found to contain an additional C-methylation domain (yielding an additional α-methyl side chain, as in epothilone). The makeup of the PKS, therefore, determines the choice of starter and extender acyl units incorporated, the extent of reduction at each condensation step, and the total number of units added to the chain. The wide diversity of structures of polyketides seen in nature is attributed to the diversity in PKS compositions. The PKS-directed synthesis of the aglycone component (narbonolide) of the antibiotic pikromycin is shown in FIG. 5. The pik PKS employs 6 modules (the loading domain is at the N-terminus of module 1); the loading domain and modules 1, 3, 4, 5, & 6 employs the precursor [S]-2-methylmalonyl CoA, module 2 uses malonyl CoA. (After incorporation, however, three of the side chains are inverted through a process not as yet fully understood.) The various degrees of reduction after each condensation cycle are determined by the presence of the corresponding reduction domains in each module. The cyclic nature of the product of the PKS is due to the TE domain-catalyzed nucleophilic attack of the OH generated after the first condensation cycle on the terminal thioester bond at ACP6. The structure of the polyketide narbonolide, therefore, is programmed by the pik PKS.

Engineering Polyketide Synthases

The present invention provides for a recombinant nucleic acid that encodes a polyketide synthase (PKS) of the present invention. The recombinant nucleic acid can be a double-stranded or single-stranded DNA, or RNA. The recombinant nucleic acid can encode an open reading frame (ORF) of the PKS of the present invention. The recombinant nucleic acid can also comprise promoter sequences for transcribing the ORF in a suitable host cell. The recombinant nucleic acid can also comprise sequences sufficient for having the recombinant nucleic acid stably replicate in a host cell. The recombinant nucleic acid can be replicon capable of stable maintenance in a host cell. In some embodiments, the replicon is a plasmid. The present invention also provides for a vector or expression vector comprising a recombinant nucleic acid of the present invention.

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those that integrate into the host cell genome.

The vectors may be chosen to contain control sequences operably linked to the resulting coding sequences in a manner that expression of the coding sequences may be effected in an appropriate host. Suitable control sequences include those that function in eukaryotic and prokaryotic host cells. If the cloning vectors employed to obtain PKS genes encoding derived PKS lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for single cell cultures of various types of organisms are well known in the art. Control systems for expression in yeast are widely available and are routinely used. Control elements include promoters, optionally containing operator sequences, and other elements depending on the nature of the host, such as ribosome binding sites. Particularly useful promoters for prokaryotic hosts include those from PKS gene clusters that result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433; hereby incorporated by reference), can be used.

As noted, particularly useful control sequences are those which themselves, or with suitable regulatory systems, activate expression during transition from growth to stationary phase in the vegetative mycelium. Illustrative control sequences, vectors, and host cells of these types include the modified *S. coelicolor* CH999 and vectors described in PCT publication no. WO 96/40968 and similar strains of *S. lividans*. See U.S. Pat. Nos. 5,672,491; 5,830,750; 5,843,718; and 6,177,262, each of which is hereby incorporated by reference. Other regulatory sequences may also be desirable which allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The various PKS nucleic acid sequences or nucleotide sequences, or a mixture of such sequences, can be cloned into one or more recombinant vectors as individual cassettes, with separate control elements or under the control of a single promoter. The PKS subunits or components can include flanking restriction sites to allow for the easy deletion and insertion of other PKS subunits. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

Of the more than thirty PKSs examined, the correspondence between use of modules in the biosynthesis and the structure of the polyketide produced is fully understood both at the level of the protein sequence of the PKS and the DNA sequence of the corresponding genes. The programming of modules into polyketide structure can be identified by sequence determination. It is possible to clone (or synthesize) DNA sequences corresponding to desired modules and transfer them as fully functioning units to heterologous, otherwise non-polyketide producing hosts such as *E. coli* (B. A. Pfeifer, S. J. Admiraal, H. Gramajo, D. E. Cane, C. Khosla, *Science* 291, 1790 (2001); hereby incorporated by reference) and *Streptomyces* (C. M. Kao, L. Katz, C. Khosla, *Science* 265, 509 (1994); hereby incorporated by reference). Additional genes employed for polyketide biosynthesis have also been identified. Genes that determine phosphopantetheine:protein transferase (PPTase) that transfer the 4-phosphopantetheine co-factor of the ACP domains, commonly present in polyketide producing hosts, have been cloned in *E. coli* and other hosts (K. J. Weissman, H. Hong, M. Oliynyk, A. P. Siskos, P. F. Leadlay, *Chembiochem* 5, 116 (2004); hereby incorporated by reference). Moreover, genes for the production of precursors such as methylmalonyl CoA and ethylmalonyl CoA have also been identified and cloned in heterologous hosts. It is also possible to re-program polyketide biosynthesis to produce a compound of desired structure by either genetic manipulation of a single PKS or by construction of a hybrid PKS composed of modules from two or more sources (K. J. Weissman, H. Hong, M. Oliynyk, A. P. Siskos, P. F. Leadlay, *Chembiochem* 5, 116 (2004); hereby incorporated by reference).

Recombinant methods for manipulating modular PKS genes to make the PKSs of the present invention are described in U.S. Pat. Nos. 5,672,491; 5,843,718; 5,830,750; 5,712,146; and 6,303,342; and in PCT publication nos. WO 98/49315 and WO 97/02358; hereby incorporated by reference. A number of genetic engineering strategies have been used with various PKSs to demonstrate that the structures of polyketides can be manipulated to produce novel polyketides (see the patent publications referenced supra and Hutchinson, 1998, Curr Opin Microbiol. 1:319-329, and Baltz, 1998, Trends Microbiol. 6:76-83; hereby incorporated by reference). In some embodiment, the components of the hybrid PKS are arranged onto polypeptides having interpolypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication no. WO 00/47724, hereby incorporated by reference.

The vast number of polyketide pathways that have been elucidated provide a host of different options to produce these carboxylic acids and lactones of the present invention as shown in Tables 1-7, and compounds 51-53. While the products can be vastly different in size and functionality, all employ virtually the same strategy for biosynthesis. The exact interfaces between non-cognate enzyme partners will be determined on a case-by-case basis. ACP-linker-KS and ACP-linker-TE regions from the proteins of interest will be aligned to examine the least disruptive fusion point for the hybrid synthase. Genetic constructions will employ sequence and ligation independent cloning (SLIC) so as to eliminate the incorporation of genetic "scarring".

A partial list of sources of PKS sequences that can be used in making the PKSs of the present invention, for illustration and not limitation, includes Ambruticin (U.S. Pat. No. 7,332,576); Avermectin (U.S. Pat. No. 5,252,474; MacNeil et al., 1993, Industrial Microorganisms: Basic and Applied Molecular Genetics, Baltz, Hegeman, & Skatrud, eds. (ASM), pp. 245-256; MacNeil et al., 1992, Gene 115: 119-25); Candicidin (FR0008) (Hu et al., 1994, Mol. Microbiol. 14: 163-72); Epothilone (U.S. Pat. No. 6,303,342); Erythromycin (WO 93/13663; U.S. Pat. No. 5,824,513; Donadio et al., 1991, Science 252:675-79; Cortes et al., 1990, Nature 348:176-8); FK506 (Motamedi et al., 1998, Eur. J. Biochem. 256:528-34; Motamedi et al., 1997, Eur. J. Biochem. 244:74-80); FK520 or ascomycin (U.S. Pat. No. 6,503,737; see also Nielsen et al., 1991, Biochem. 30:5789-96); Jerangolid (U.S. Pat. No. 7,285,405); Leptomycin (U.S. Pat. No. 7,288,396); Lovastatin (U.S. Pat. No. 5,744,350); Nemadectin (MacNeil et al., 1993, supra); Niddamycin (Kakavas et al., 1997, J. Bacteriol. 179:7515-22); Oleandomycin (Swan et al., 1994, Mol. Gen. Genet. 242:358-62; U.S. Pat. No. 6,388,099; Olano et al., 1998, Mol. Gen. Genet. 259:299-308); Oligomycin (Omura, S., Ikeda, H., Ishikawa, J., 2001, Proc. Natl. Acad. Sci. USA 98:12215-12220); Pederin (PCT publication no. WO 2003/044186); Pikromycin (Xue et al., 2000, Gene 245:203-211); Pimaricin (PCT publication no. WO 2000/077222); Platenolide (EP Pat. App. 791,656); Rapamycin (Schwecke et al., 1995, Proc. Natl. Acad. Sci. USA 92:7839-43); Aparicio et al., 1996, Gene 169:9-16); Rifamycin (August et al., 1998, Chemistry & Biology, 5: 69-79); Soraphen (U.S. Pat. No. 5,716,849; Schupp et al., 1995, J. Bacteriology 177: 3673-79); Spiramycin (U.S. Pat. No. 5,098,837); Tylosin (EP 0 791,655; Kuhstoss et al., 1996, Gene 183:231-36; U.S. Pat. No. 5,876,991). Additional suitable PKS coding sequences are readily available to one skilled in the art, or remain to be discovered and characterized, but will be available to those of skill (e.g., by reference to GenBank). Each of the references cited is hereby specifically and individually incorporated by reference.

Complex polyketides comprise a large class of natural products that are synthesized in bacteria (mainly members actinomycete family; e.g. *Streptomyces*), fungi and plants. Polyketides form the aglycone component of a large number of clinically important drugs, such as antibiotics (e.g. erythromycin, tylosin), antifungal agents (e.g. nystatin), anticancer agents (e.g. epothilone), immunosuppressives (e.g. rapamycin), etc. Though these compounds do not resemble each other either in their structure or their mode of action, they share a common basis for their biosynthesis, which is carried out by a group of enzymes designated polyketide synthases.

The assembly of a loading module and up to two extender modules can be done in *E. coli*. Compounds requiring acetyl CoA and malonyl CoA as precursors can be made in *E. coli* hosts. The modules can also be cloned in vectors that can be introduced into a variety of *Streptomyces* hosts (e.g. *Streptomyces coelicolor*).

Compounds requiring propionate (methylmalonate) precursors can be made in a variety of *Streptomyces* hosts which have ample supplies of these precursors. Alternatively, *E. coli* can be fed with propionate and the enzyme methylmalonyl CoA mutase can be cloned in an *E. coli* host engineered to incorporate vitB12.

Compounds which require module J for their synthesis will contain an ethyl side chain and will employ 2-ethylmalonyl CoA as a precursor. Ethylmalonate is produced from the isomerization of butyrate. The genes encoding the enzymes in this pathway to produce this precursor can be cloned into in a suitable *E. coli* Numerous streptomycetes exist that produce ethylmalonyl CoA, some of which are suitable for cloning and expression of PKS genes (e.g. *Streptomyces fradiae*).

It is probably unwise to use *E. coli* to produce the constructs required for the biosynthesis of molecules requiring three or more modules for their syntheses. Three modules would comprise 15 kb or more. The Izumenolide PKS is a good choice for the synthesis of these compounds, and manipulation of the PKS in situ in the chromosome of the host, *Micromonospora chalcea* subsp. *izumensis*.

Host Cells

The present invention provides for a host cell comprising any of the recombinant nucleic acid and/or PKS of the present invention. The host cell can be a genetically modified host cell. The host cell, when cultured, is capable of producing any of the carboxylic acids or lactones of the present invention, including but not limited to those of compounds 1-53. In some embodiments, the host cell, when cultured, is capable of producing a carboxylic acid described in Tables 1 and 2, and a lactone described in Tables 3-7. The host cell can be a eukaryotic or a prokaryotic cell.

The host cells of the present invention are genetically modified in that heterologous nucleic acid have been introduced into the host cells, and as such the genetically modified host cells do not occur in nature. The suitable host cell is one capable of expressing a nucleic acid construct encoding a PKS capable of biosynthesis of a carboxylic acid or lactone. The recombinant nucleic acid encoding the PKS is operatively linked to a heterologous promoter and one or more control regions which result in expression of the PKS in the host cell.

Any prokaryotic or eukaryotic host cell may be used in the present method so long as it remains viable after being transformed with a sequence of nucleic acids. Generally, although not necessarily, the host microorganism is bacterial.

Examples of bacterial host cells include, without limitation, those species assigned to the *Escherichia, Enterobacter, Azotobacter, Erwinia, Bacillus, Pseudomonas, Klebsiella, Proteus, Salmonella, Serratia, Shigella, Rhizobia, Vitreoscilla*, and *Paracoccus* taxonomical classes. Preferably, the host cell is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "crosstalk" (i.e., interference) occur between the host cell's own metabolic processes and those processes involved with the mevalonate pathway. Suitable prokaryotic cells include *Escherichia coli, Pseudomonas putida*, or *Streptomyces* species.

Suitable eukaryotic cells include, but are not limited to, fungal, insect or mammalian cells. Suitable eukaryotic cells include yeast cells, such as from the genus *Saccharomyces* or *Schizosaccharomyces*. A suitable species from the genus *Saccharomyces* is *Saccharomyces cerevisiae*. A suitable species from the genus *Schizosaccharomyces* is *Schizosaccharomyces pombe*.

Methods of Producing Carboxylic Acids or Lactones Using the PKSs of the Present Invention The present invention provides a method of producing a carboxylic acid of the present invention, such as a carboxylic acid described in Tables 1 and 2 and compounds 51-53, comprising: providing a host cell of the present invention, and culturing said host cell in a suitable culture medium such that the carboxylic acid is produced. The method can further comprise isolating said carboxylic acid from the host cell and/or the culture medium. The method can further comprise reacting the carboxylic acid with an alcohol to produce an ester.

The step of isolating said carboxylic acid from the host cell and/or the culture medium can comprise reducing the pH of the culture medium to about 3.5 and extracting the carboxylic acid from the culture medium using a suitable solvent. Suitable solvents include ethylacetate, amylacetate, tetrahydrofuran, and the like. The carboxylic acid is then reextracted into water at neutral pH and then further purified by ion-exchange chromatography, HPLC, or the like. The acids could be converted to esters for use as biofuels. This would also remove the need for pH adjustment during extraction.

Linear carboxylates can be esterified by heating them with alcohols in the presence of an acid catalyst. Suitable acid catalysts are well know to those skilled in the art. A suitable acid catalyst is concentrated sulfuric acid. The esterification reaction is both slow and reversible, thus the ester is generally distilled off to prevent reformation of the acid. Suitable methods of esterification are well know to those skilled in the art. The equation for the reaction between an acid RCOOH and an alcohol R'OH (where R and R' can be the same or different) is:

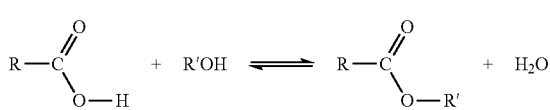

The present invention provides a method of producing a lactone of the present invention, such as a lactone described in Tables 3-7, comprising: providing a host cell of the present invention, and culturing said host cell in a suitable culture medium such that the lactone is produced. The method can further comprise isolating said lactone from the host cell and/or the culture medium.

Lactones are generally excreted from the cells into the surrounding medium. The step of isolating said lactone from the host cell and/or the culture medium can comprise extracting the lactone from the culture medium using a suitable solvent at neutral pH and concentrating the lactone by drying the solvent phase. Suitable solvents include ethylacetate, amylacetate, tetrahydrofuran, and the like. The lactone can be further purified by reversed-phase chromatography, HPLC, or the like.

The method can further comprise oxidizing or combusting a combustible composition comprising the ester and/or lactone, or a mixture thereof, isolated from the host cell to obtain energy. In some embodiments, the oxidizing or combusting is complete or substantially complete. In some embodiments, the energy obtained is heat energy and/or increased pressure. In some embodiments, the oxidizing or combusting takes place in an engine. The engine can be any engine that oxidizes or combusts a fuel to obtain energy, such as an internal combustion engine, external combustion engine, jet engine, furnace, boiler, or the like.

A variety of methods for heterologous expression of PKS genes and host cells suitable for expression of these genes and production of polyketides are described, for example, in U.S. Pat. Nos. 5,843,718; 5,830,750 and 6,262,340; WO 01/31035, WO 01/27306, and WO 02/068613; and U.S. Patent Application Pub. Nos. 20020192767 and 20020045220; hereby incorporated by reference.

The present invention provides for a composition comprising a carboxylic acid or lactone, or an ester derived from the carboxylic acid, isolated from a host cell, from which the carboxylic acid or lactone was produced, and/or the culture medium, and trace residues and/or contaminants of the host cell and/or the culture medium.

Isolating the carboxylic acid or lactone involves the separating at least part or all of the host cells and/or culture medium, and parts thereof, from which the carboxylic acid or lactone was produced, from the carboxylic acid or lactone. The isolated carboxylic acid or lactone may be free or essentially free of impurities formed from at least part or all of the host cells and/or culture medium, and parts thereof. The isolated carboxylic acid or lactone is essentially free of these impurities when the amount and properties of the impurities do not interfere in the use of the composition as a fuel, such as a fuel in a combustion reaction. These host cells are specifically cells that do not in nature produce the carboxylic acid or lactone.

The present invention also provides for a combustible composition comprising an isolated ester or lactone and cellular components, wherein the cellular components do not substantially interfere in the combustion of the composition. The cellular components include whole cells or parts thereof. The cellular components are derived from host cells which produced the carboxylic acid, from which the ester is derived, or lactone.

The ester or lactone of the present invention are useful as fuels as chemical source of energy that can be used as an alternative to petroleum derived fuels, ethanol and the like. The carboxylic acid or lactone of the present invention are also useful in the synthesis of alkanes, alcohols, and esters of various for use as a renewable fuel. In addition, the carboxylic acid or lactone can also be as precursors in the synthesis of therapeutics, or high-value oils, such as a cocoa butter equivalent. The carboxylic acid or lactone are also useful in the production of the class of eicosanoids or related molecules, which have therapeutic related applications.

The combustible composition can further comprise one or more hydrocarbons, or a mixture thereof, capable of oxidation or combustion, such as a biofuel, fossil fuel, or the like.

The invention having been described, the following examples are offered to illustrate the subject invention by way of illustration, not by way of limitation.

EXAMPLE 1

Cloning scheme of PKSs for producing six-membered lactones

The six-membered lactones of the present invention can be produced using the following described method.

The loading domain (LD) and first extension module from previously characterized pathways is coupled to a module that will saturate the first extender and incorporate the next desired extender unit. The thioesterase (TE) from the erythromycin biosynthesis pathway is shown to be quite adept at cyclizing 6-membered lactones. Therefore, this TE is used to cyclize all of these initial products. This approach limits the number of unnatural intermodular junctions to two per construct. One of these (the addition of the TE) is well documented and well know to those skilled in the art.

The pathways are as follows; the Spiramycin cluster from *Streptomyces ambofaciens* (the niddamycin pathway from *Streptomyces caelestis* can also serve this purpose) is used for an acetate starter and one acetate extension. The chalcomycin pathway from *Streptomyces bikiniensis* is used to load acetate and extend propionate. The spinosad pathway from *Saccharapolyspora spinosa* is used to incorporate a propionate starter and an acetate extension. The tylosin pathway from *Streptomyces fradiae* is used to initiate and extend with propionate. The nystatin pathway from *S. noursei* provides a means to incorporate an additional acetate and saturate the carbonyl of the previous extension. The erythromycin pathway from *Saccharopolyspora erythraea* provides a propionate extension and reduction of the penultimate carbonyl as well as the thioesterase to be used in all constructs.

The following strains can be obtained from national culture collections: *Streptomyces ambofaciens* ATCC 23877, *S. caelestis* NRRL-2821, *S. bikiniensis* NRRL2737, *Saccharapolyspora spinosa* NRRL18538 and 18823, *S. fradiae* ATCC 19609, *S. noursei* ATCC 11455, and *Saccharopolyspora erythraea* ATCC 11635.

The initial genetic constructs are built in two vectors for *E. coli* and two for *Streptomyces coelicolor*. Specifically, these are pPRO18 (propionate inducible) and pET28 (IPTG inducible) for *E. coli*, and pOJ446 (cytoplasmic) and pSET152 (integrating) for *S. coelicolor*. The ErmE* and Tet promoters are used in the *Streptomyces* constructs to explore constitutive and inducible expression, respectively. Because *E. coli* does not produce the essential building block methylmalonate, the BAP1 strain is used as a host. Alternatively a plasmid-based system capable of converting succinyl-CoA to methylmalonate can also be used.

Figure 6:
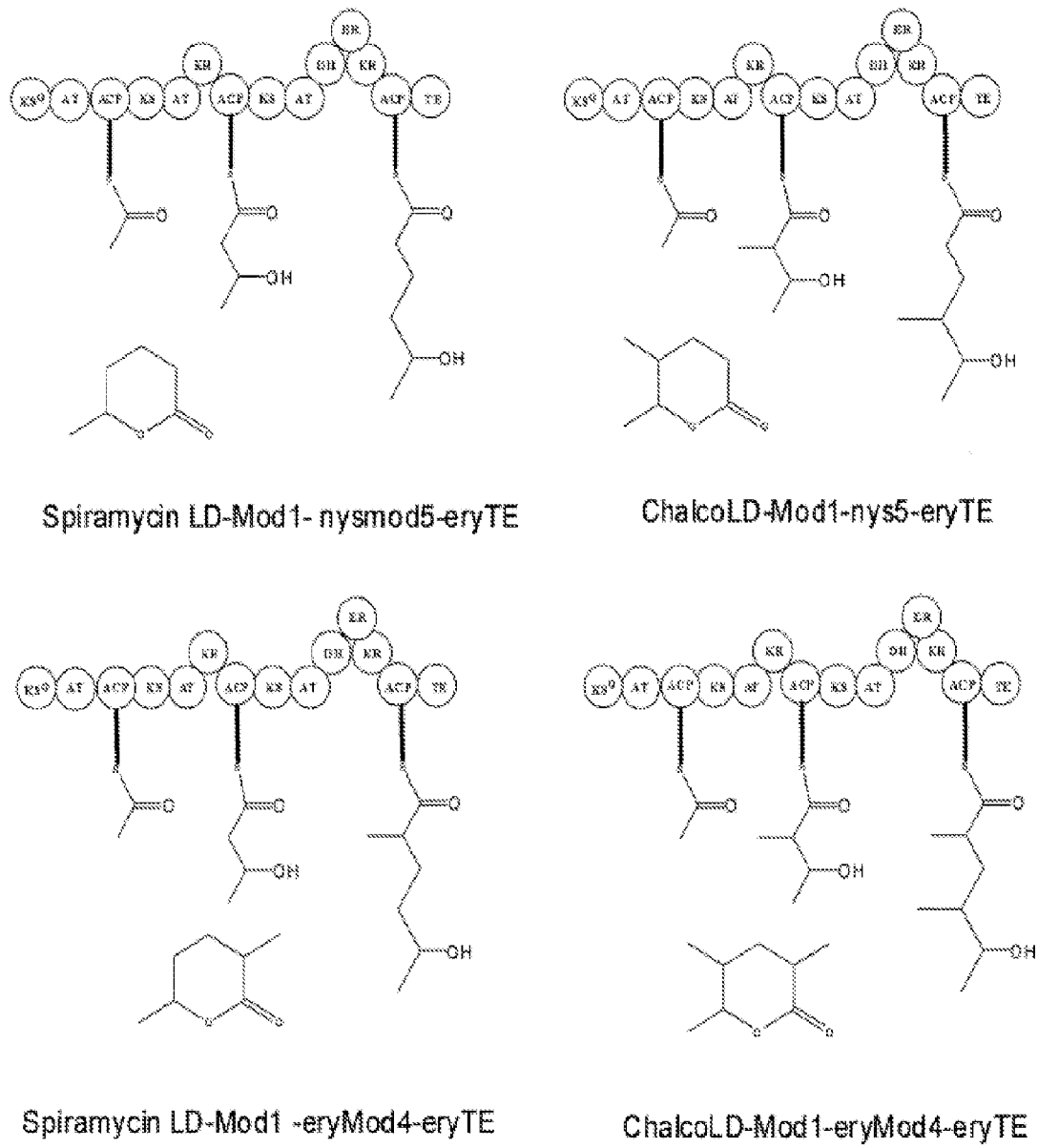
FIG. 6 shows exemplary PKSs for synthesizing lactone compounds 26, 27, 29, and 30.
Figure 7:
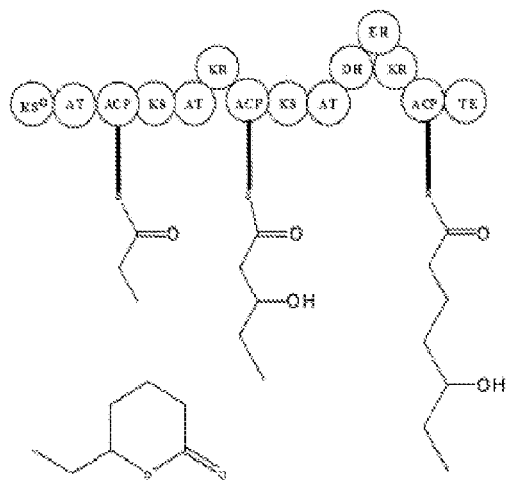
FIG. 7 shows exemplary PKSs for synthesizing lactone compounds 32, 35, 37, and 38.
Figure 7:
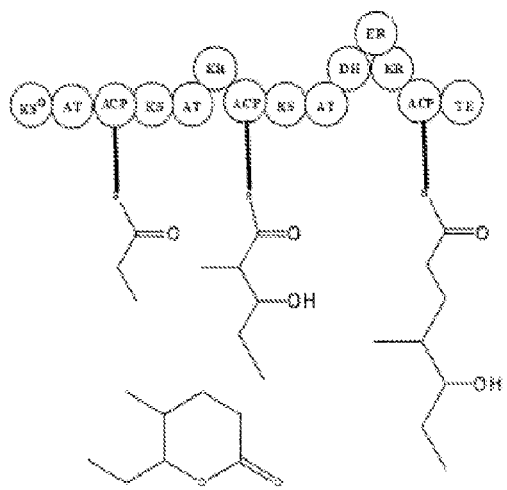
Figure 7:
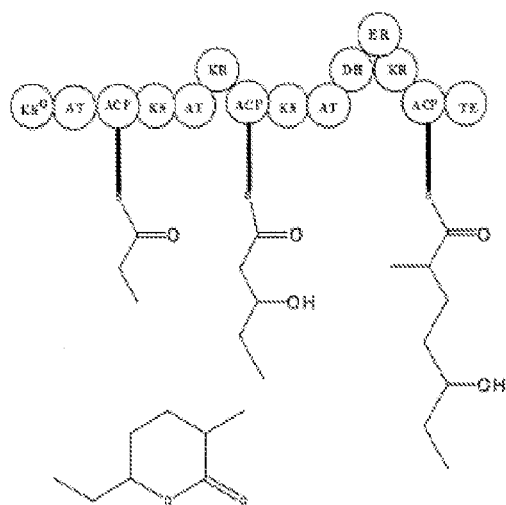
Figure 7:
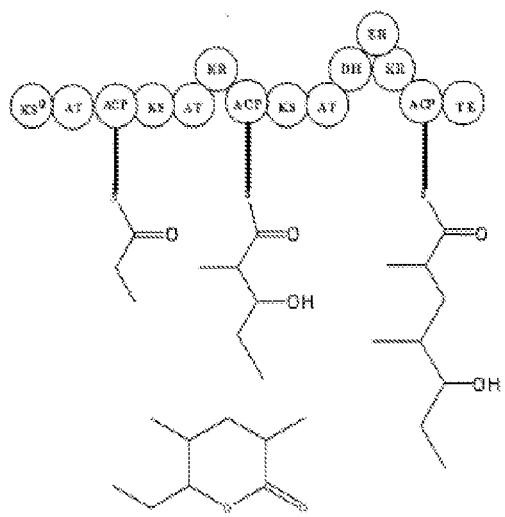

All constructs are designed to produce a single protein capable of catalyzing all of the steps necessary to convert the building blocks malonyl-CoA and/or methylmalonyl-CoA into the desired products. In the biosynthesis scheme illustrated in FIGS. 6 and 7, this requires two non-native interactions per construct. In all cases these are between the first and second extension modules and again between the second extension module and the thioesterase. In the constructs described, the loading domain, first extension module and (in most cases) the ketosynthase domain from the second extension module are all derived from a single pathway. The exceptions are those constructs containing the loading domain and first extension from the spinosad pathway. These two modules exist as a single enzyme. Therefore, to avoid the problems of protein-protein interaction, a linker peptide is introduced to fuse this enzyme to the downstream portion of the target complex.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A method of producing a carboxylic acid of Formula (I),

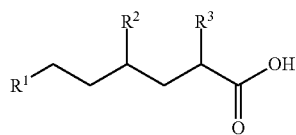

(I)

wherein $R^1$ is H or —$CH_3$; $R^2$ is H, —$CH_3$, or —$CH_2CH_3$; and $R^3$ is H, —$CH_3$, or —$CH_2CH_3$; or $R^2$ and $R^3$ are each H, and $R^1$ is H, —$CH_3$, or —$(CH_2)_n CH_3$, where n is an integer from 1 to 6; and wherein the method comprises culturing a host cell comprising a vector encoding a non-naturally occurring polyketide synthase in a culture medium under conditions where the PKS is expressed and the carboxylic acid is produced, wherein the PKS comprises a loading domain and two or more extender modules, and the PKS is a hybrid PKS comprising a combination of modules which in nature are not found in this combination.

2. The method of claim 1, wherein the carboxylic acid has a structure where $R^1$ is H or —$CH_3$; $R^2$ is H, —$CH_3$, or —$CH_2CH_3$; and $R^3$ is H, —$CH_3$, or —$CH_2CH_3$.

3. The method of claim 1, wherein the carboxylic acid has a structure where $R^2$ and $R^3$ are each H, and $R^1$ is H, —$CH_3$, or —$(CH_2)_n CH_3$, where n is an integer from 1 to 6.

4. The method of claim 3, wherein the carboxylic acid has a structure where $R^2$ and $R^3$ are each H, and $R^1$ is —$(CH_2)_n CH_3$, where n is an integer from 1 to 6.

5. The method of claim 1, wherein the carboxylic acid has a structure disclosed in Tables 1 and 2.

6. The method of claim 1, further comprising: (c) isolating said carboxylic acid from the host cell and/or the culture medium.

7. The method of claim 6, further comprising: (d) reacting the isolated carboxylic acid with an alcohol to produce an ester.

8. A method of producing a lactone of Formula (II),

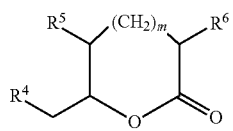

(II)

wherein $R^4$ is H or —$CH_3$; and $R^5$ and $R^6$ are each independently H, —$CH_3$, or —$CH_2CH_3$; and m is 1, 3, 5, 7, or 9; with the proviso that when m is 3, 5, 7, or 9, then $R^4$ is H or —$CH_3$ and $R^5$ and $R^6$ are each H; and wherein the method comprises culturing a host cell comprising a vector encoding a non-naturally occurring polyketide synthase in a culture medium under conditions where the PKS is expressed and the lactone is produced, wherein the PKS comprises a loading domain, two or more extender modules, and a thioesterase domain positioned 3' to the terminal extender module, and the PKS is a hybrid PKS comprising a combination of modules which in nature are not found in this combination.

9. The method of claim 8, wherein the lactone has a structure where m is 1 and $R^5$ and $R^6$ are each independently H, —$CH_3$, or —$CH_2CH_3$.

10. The method of claim 8, wherein the lactone has a structure where m is 3, 5, 7, or 9; $R^4$ is H or —$CH_3$, and $R^5$ and $R^6$ are each H.

11. The method of claim 8, wherein the lactone is any lactone disclosed in Tables 3-7.

12. The method of claim 8, wherein the lactone is a six-membered lactone having the following chemical structure:

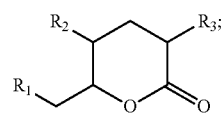

(III)

wherein $R^1$ is H or —$CH_3$; and $R^2$ and $R^3$ are each independently H, —$CH_3$, or —$CH_2CH_3$.

13. The method of claim 8, wherein the lactone is an eight-membered lactone having the following chemical structure:

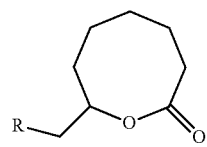

(IV)

wherein R is H or —$CH_3$.

14. The method of claim 8, wherein the lactone is a ten-membered lactone having the following chemical structure:

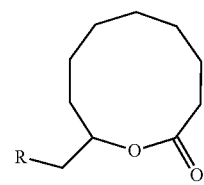

(V)

wherein R is H or —$CH_3$.

15. The method of claim 8, wherein the lactone is a twelve-membered lactone having the following chemical structure:

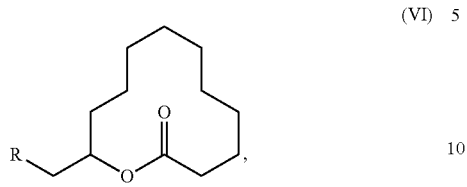
(VI)

wherein R is H or —CH$_3$.

16. The method of claim 8, wherein the lactone is a fourteenmember lactone having the following chemical structure:

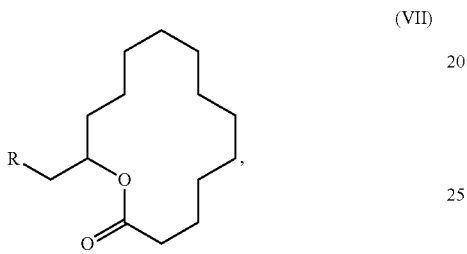
(VII)

wherein R is H or —CH$_3$.

17. The method of claim 8, further comprising: (c) isolating said lactone from the host cell and/or the culture medium.

* * * * *